(12) United States Patent
Jensen (10) Patent No.: US 6,390,817 B1
(45) Date of Patent: May 21, 2002

(54) FIBER TIPPED DENTAL SUBSTANCE APPLICATOR

(76) Inventor: Steven Jensen, 1190 W. Chavez Dr., So. Jordan, UT (US) 84095

( * ) Notice: Subject to any disclaimer, the term of this patent is extended or adjusted under 35 U.S.C. 154(b) by 0 days.

(21) Appl. No.: 09/858,052

(22) Filed: May 15, 2001

(51) Int. Cl.[7] ................................................. A61C 5/04
(52) U.S. Cl. ........................................ 433/89; 604/311
(58) Field of Search ............................. 433/89, 90, 80; 604/310, 311; 401/265

(56) References Cited

U.S. PATENT DOCUMENTS

| | | | | |
|---|---|---|---|---|
| 4,997,371 A | * | 3/1991 | Fischer | 433/90 |
| 5,269,684 A | * | 12/1993 | Fischer | 433/90 |
| 5,816,804 A | * | 10/1998 | Fischer | 433/90 |
| 6,059,570 A | * | 5/2000 | Dragan et al. | 433/90 |
| 6,038,002 A | * | 7/2000 | Martin et al. | 433/90 |
| 6,238,120 B1 | * | 5/2001 | Mark | 401/265 |

* cited by examiner

*Primary Examiner*—John J. Wilson
*Assistant Examiner*—Melba Bumgarner
(74) *Attorney, Agent, or Firm*—Daniel McCarthy (57) ABSTRACT

A fiber tipped dental substance applicator that is insertable into a bore of an exit orifice of a syringe. The applicator may include one or more fluid passageways through which a dental substance may flow from the syringe to fibers at the end of the applicator. The tip may include a flocked smoothing bulb.

8 Claims, 9 Drawing Sheets

FIBER TIPPED DENTAL SUBSTANCE APPLICATOR

BACKGROUND OF INVENTION

The invention relates to applicators for applying dental substances to dental surfaces such as teeth. Many dental substances, such as pit and fissure sealants and bonding agents and acid etches and the like, require precise and artful manual application to a dental surface in order to achieve the desired aesthetic and functional result. The invention relates to a dental substance applicator with a fiber tip to achieve such desired results.

In the prior art, some dental substances such as pit and fissure sealants and bonding could be applied to teeth by use of a brush or swab. Such application was successful but time consuming and inefficient and did not always achieve the optimal aesthetic or functional result that the patient and the dental care provider would hope for. In particular, the seal achieved by such techniques was not always optimal.

Advances were made by providing a squeezable vial, an ejector gun or a syringe as a dental substance reservoir and an applicator tip with flocking to apply the dental substance to a dental surface. Disposable applicators with a flocked tip are available from Microbrush Corporation of Clearwater, Fla. Applicators with a flocked tip were an advance over the prior art brush or swab devices because they allowed a dental substance to be both dispensed and applied with the flocking with one hand without need to change tools. However, because the flocking was only around the exterior periphery of the applicator, dispensing of a dental substance and its actual application to a dental surface by spreading it out with the flocking was performed in two separate steps and still did not achieve optimal aesthetic and functional results. Examples of prior art applicators with flocked tips are found in U.S. Pat. Nos. 6,059,570 and 6,083,002 which are hereby incorporated by reference.

There was some effort in the prior art to cause dental substances to flow through a brush end so that the dental substance could be applied to a dental surface simultaneously with dispensing of the dental substance from a reservoir. However, filled dental substances were found to clog the brush end right away, rendering such devices useless. For the purposes of this document "filled" dental substances means a dental substance or restorative material with floating particles in it. For example, in a filled dental composite, glass particles will be found between resin molecules to provide a fracture resistant and more wear resistant restoration.

In order to achieve a superior fiber tipped applicator for use with filled materials, one inventor designed a spiral applicator tip in which the dental substance traveled around the fibers along a helical path in order to avoid clogging the fibers. At the applicator end, the dental substance was dispensed adjacent the fibers. Clogging was avoided, but merely dispensing the dental substance adjacent the fibers was still not optimal. Further, the helical pathway was complex and unnecessarily expensive, having marketing appeal but lacking in scientific benefits. An example of such a device is depicted in U.S. Pat. No. 5,269,684 which is hereby incorporated by reference. Another disadvantage of this type of tip is that it is conical in shape progressing from a wide dimension at the reservoir end to a narrow dimension at the exit orifice. However, the conical shape tends to be inconvenient for the dental care provider, preventing the applicator from being placed exactly where it is desired to be used.

Another effort in the prior art was to provide an applicator tip with bristles about the exterior of a dispensing orifice with bristles oriented in the direction of flow of a dental substance through the dispensing orifice. However, such a structure was only a minor advance over flocked tips of the prior art. An example of such a device is found in U.S. Pat. No. 5,816,804 which s hereby incorporated by reference.

There remains a need for a fiber tipped dental substance applicator which does not clog when presented with a filled material, which closely juxtaposes dispensed dental substance with fibers for which, accurate and artful application by a dental care provider, and which is sized and shaped for convenience of use.

SUMMARY OF INVENTION

In some embodiments of the invention, a fiber tipped dental substance applicator is provided that closely juxtaposes fibers with dental substances being dispensed so that dental substance may be dispensed and spread on a dental surface in an efficient fluid motion to achieve a desired aesthetic and functional result, including a good seal.

Other objects, features and advantages of the invention will become apparent upon reading the specification and reviewing the appended drawings.

DETAILED DESCRIPTION

Figure 1:
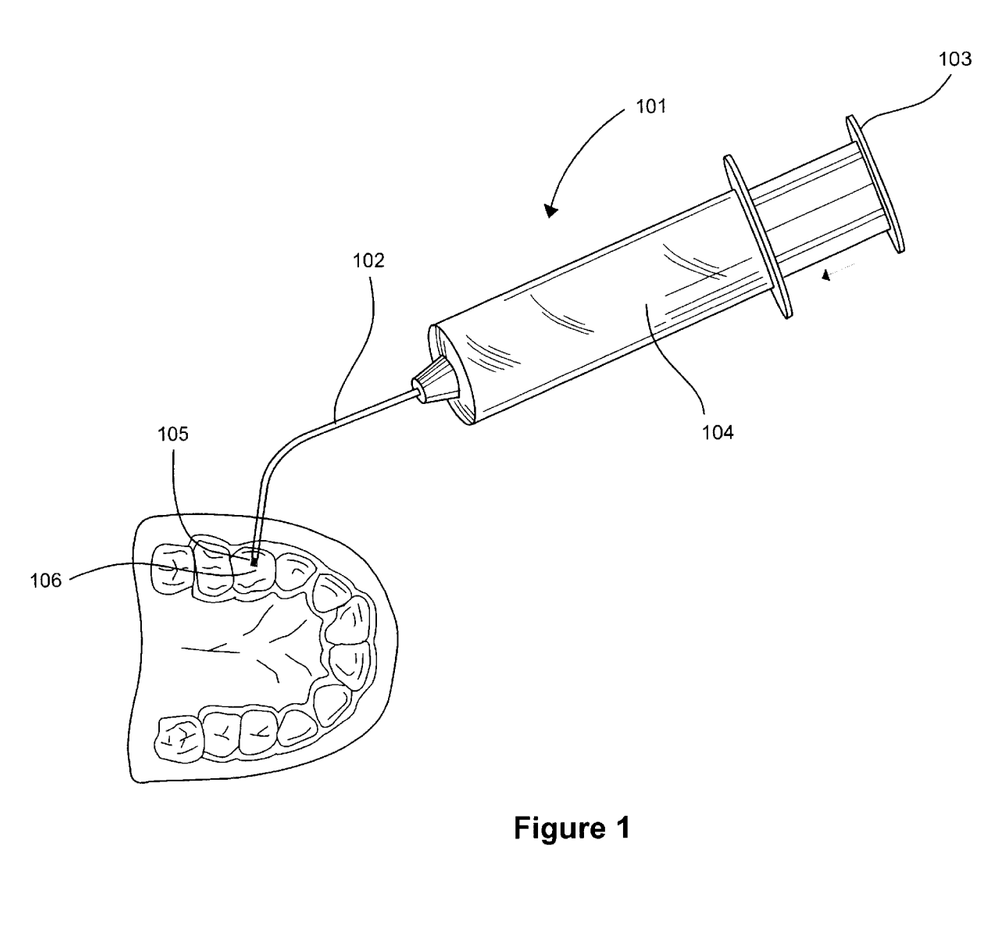
FIG. 1 depicts a syringe dispenser and a fiber tipped dental substance applicator of the invention in use on a dental surface.

Referring to FIG. 1, a single barrel syringe 101 is depicted with a fiber tipped dental substance applicator 102 installed thereon. The syringe has a reservoir 104 for holding a dental substance and a plunger 103 for exerting pressure on the dental substance in order to cause the dental substance to be forced through the applicator 102. The applicator 102 is fiber tipped 105 for spreading a dental substance on a dental surface 106 after the dental substance has been forced from reservoir through the applicator 102.

Figure 2:
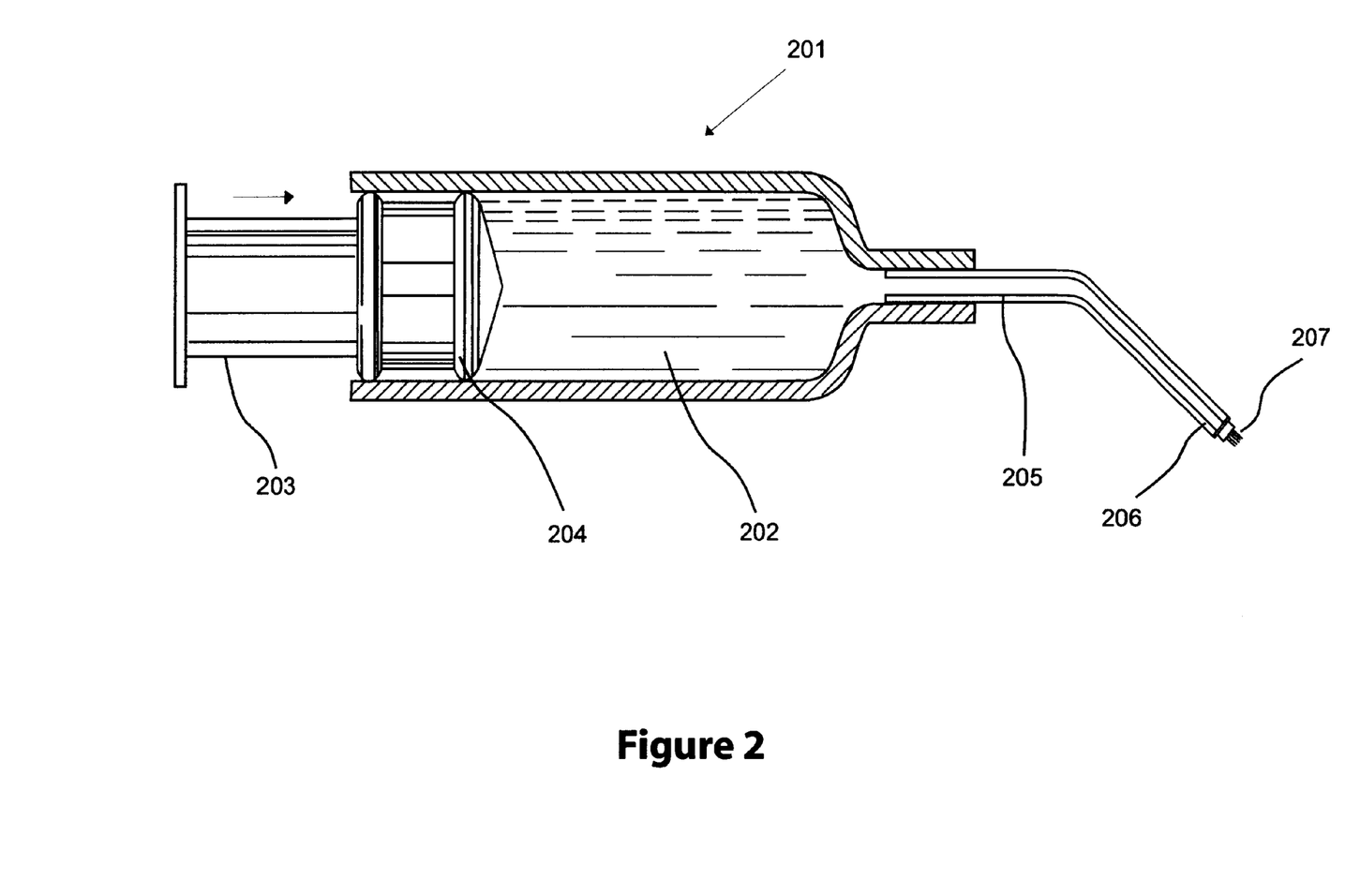
FIG. 2 depicts a cross sectional view of a syringe and fiber tipped dental substance applicator.

Referring to FIG. 2, a cross sectional view of a syringe 201 with applicator 207 of the invention is depicted. The syringe 201 includes a reservoir or chamber 202 for holding a dental substance to be dispensed. A plunger 203 is provided with seal 204 within the barrel for forcing dental substance from the reservoir 202. The dental substance travels from the reservoir through the delivery passageway 205 to delivery orifice 206. The delivery passageway 205 is preferably a metal cylinder that may be angled for desired presentation within a patient's mouth. Because the delivery passageway 205 is cylindrical, it is approximately the same dimension along its length rather than being of larger dimension at the syringe end than at the orifice. This makes it easier for the dental care provider to place it in proximity with various dental structures, hence making it more convenient to use than some prior art devices. The fiber tipped dental substance applicator 207 is held in place in the orifice 206 of the delivery passageway 205. The fiber tipped dental substance applicator has the fibers generally in its center, which will be aligned with the center of the bore of the orifice 206, and will have a plurality of recesses in it to permit dental substance to flow along the sides of the fibers. Centering the fibers along the bore is advantageous in that it makes movement of the fibers intuitive as they are used to apply a dental substance to a dental surface.

Figure 3A:
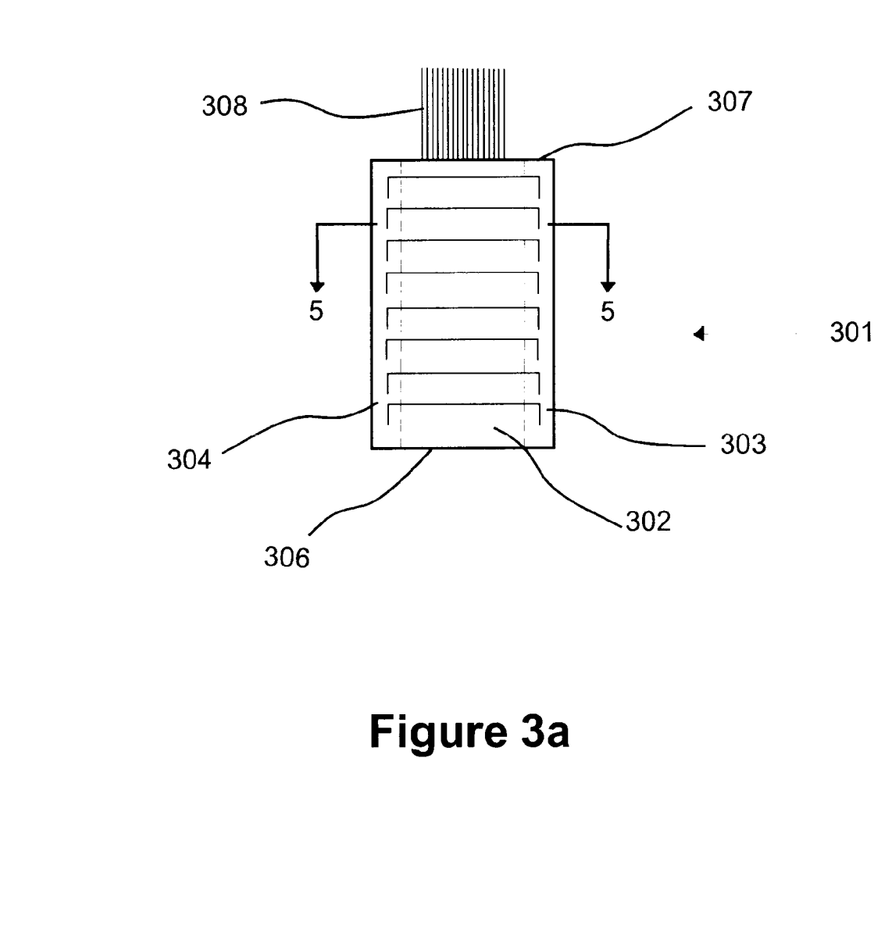
FIGS. 3a, 3b and 4 depict a side view, a perspective view and a front view of an applicator tip of the invention.
Figure 3B:
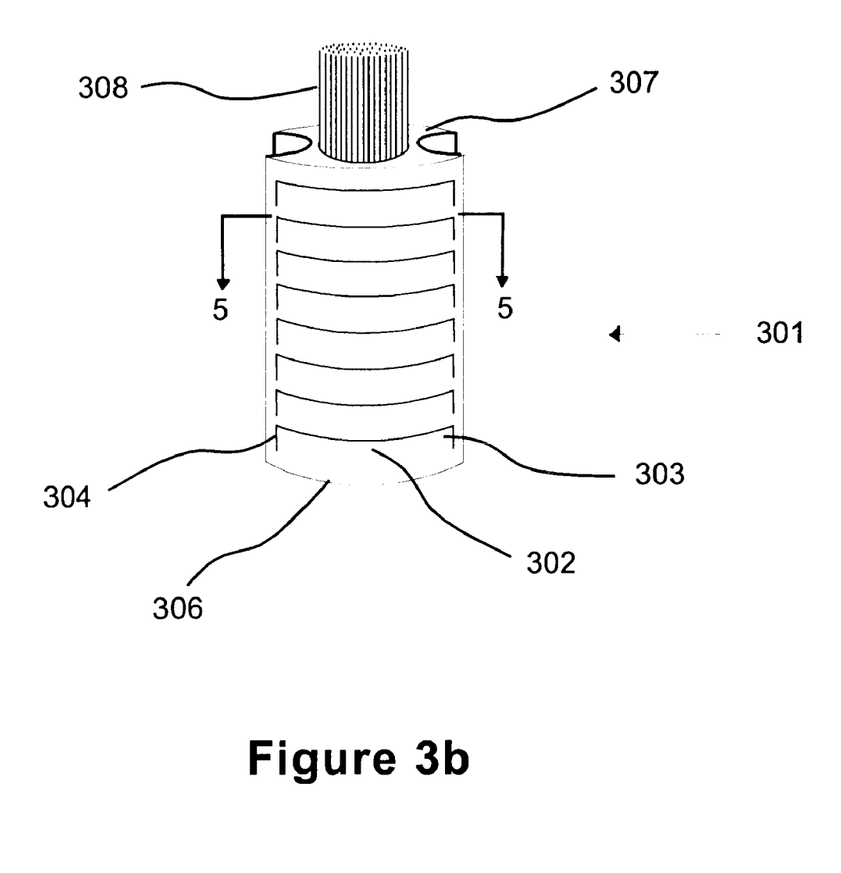

FIGS. 3a and 3b depict front and side views of a fiber tipped dental substance applicator 301 of the invention. It includes a body 302 which is generally cylindrical in shape or otherwise shaped to match the shape of the interior of the bore of the orifice 206 such as the interior of a cylindrical metal bore. The applicator 301 includes at least one pathway 303 and 304 (shown in phantom) along the outer periphery of the body 302 through which a dental substance may flow when forced from the orifice 206. It has a proximal end 306 for insertion into the bore and a distal end 307. On the distal end 307 a plurality of fibers 308 are found for applying the dental substance to a dental surface. The fibers 308 are preferably located so that they will be about in the center of the bore of the orifice 206.

Figure 4:
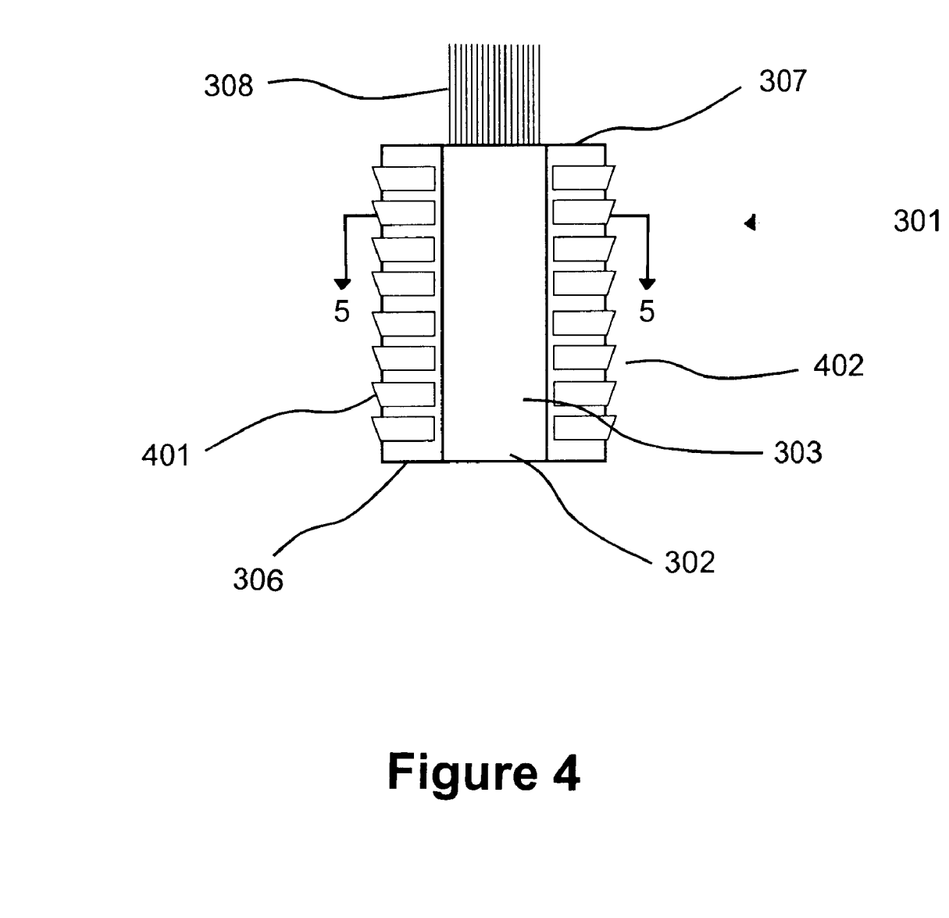

FIG. 4 depicts a side view of the fiber tipped dental substance applicator 301. From this view, only one fluid flow pathway 303 or passage is visible. Also depicted in this view are one-way locking lips or plates 401 and 402 located on the exterior periphery of the body 302 in an angular orientation, such as about 30 to 45 degrees with the vertical. The lips 401 and 402 would preferably be plastic or other flexible material and would bend out of the way as the applicator 301 is pressed into the bore. Once in the bore, however, the lips 401 and 402 serve to frictionally resist removal of the applicator 301 from the bore to avoid inadvertent detachment in a patient's mouth. Alternatively, a textured surface of the body 302 or other mechanical locking device could be used to fasten the applicator 302 in the bore.

Figure 5:
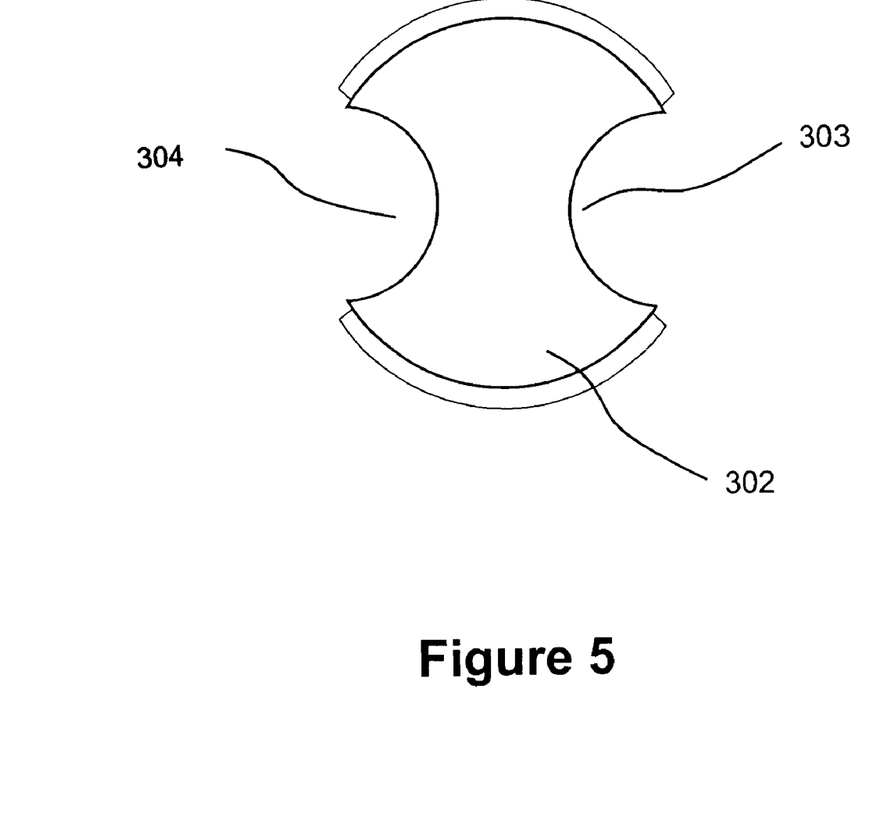
FIG. 5 depicts a cross sectional view of the applicator tip of FIGS. 3a, 3b and 4 at 5—5.

FIG. 5 is a cross sectional view of the fiber tipped dental substance applicator 301 at 5—5. It depicts the body 302 and the pathways 303 and 304.

Figure 6:
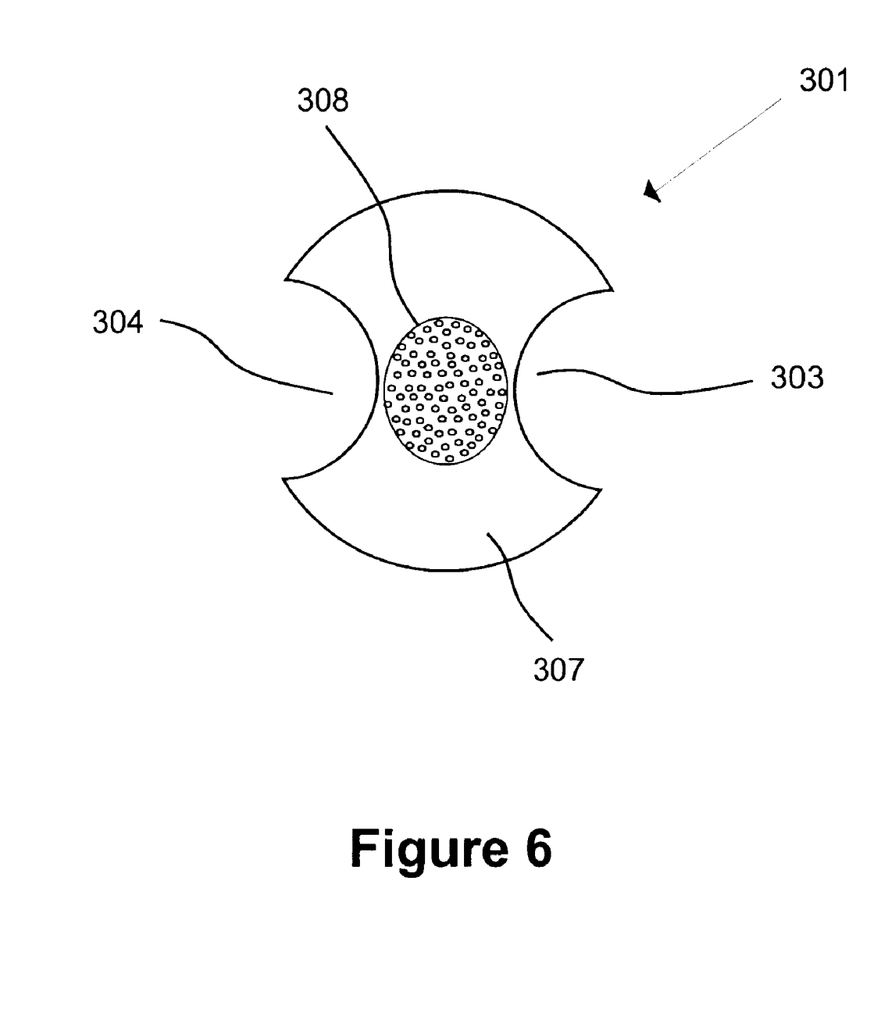
FIG. 6 depicts a distal end view of the applicator tip.

FIG. 6 depicts an end view of the fiber tipped dental substance applicator 301 from the distal end 307. The fibers 308 are shown adjacent the pathways 303 and 304.

Figure 7:
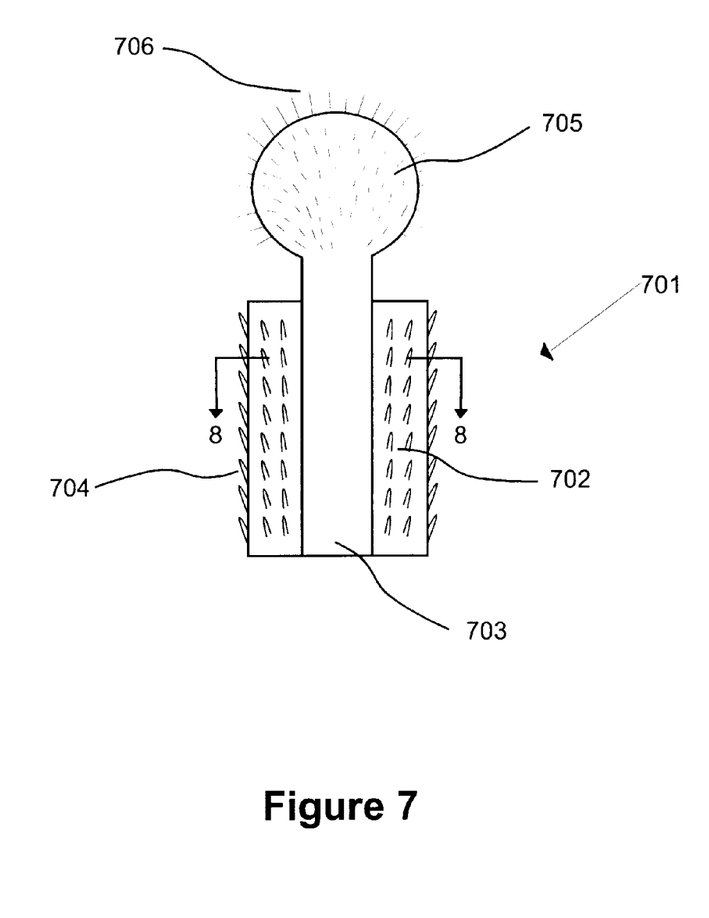
FIG. 7 depicts a side view of an alternative applicator tip of the invention.

FIG. 7 depicts a side view of an alternative applicator tip 701 of the invention. The applicator tip 701 includes a body 702 with fluid flow grooves 703 with hooks 704 for frictional engagement with a metal cylindrical orifice of a syringe. The tip 701 includes a flocked distal smoothing bulb 706 having individual flocking fibers 705 thereon for smoothing or applying a dental substance.

Figure 8:
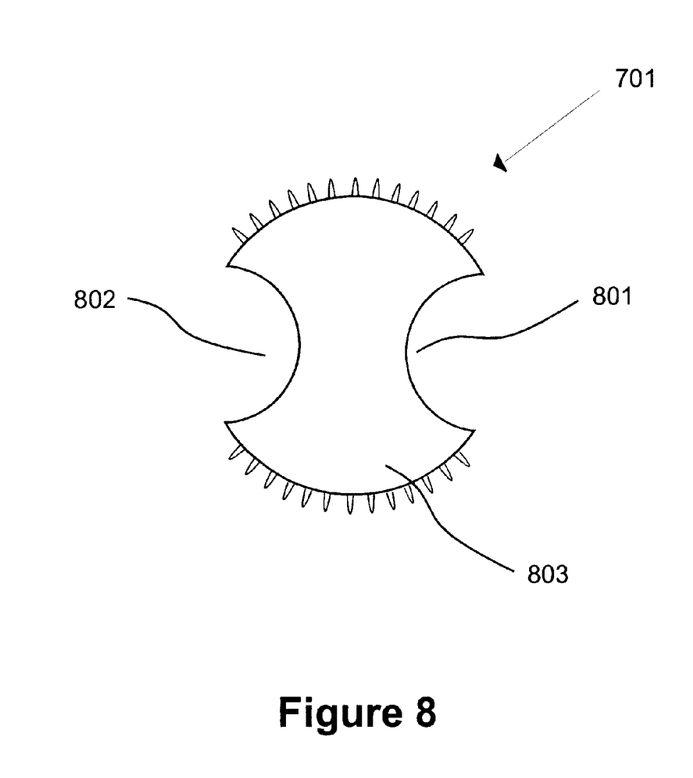
FIG. 8 depicts a cross sectional view at 8—8 from FIG. 7 of the applicator tip.

FIG. 8 depicts a cross sectional view at 8—8 from FIG. 7 of the applicator tip 701. The tip 701 includes a body 803 such as injection molded plastic with a plurality of fluid flow passages 801 and 802 through which a dental substance may flow to the smoothing bulb 706.

By providing one or more passageways adjacent the fibers or smoothing bulb, the invention permits central location of the fibers with the dental substance flowing right next to them. Clogging of the fibers by a filled material is avoided, the expense and complexity of a helical passageway is avoided, and symmetry of the passageways with respect to the fibers is maintained. As desired, there may be as many pathways as desired, preferably two or more.

The bristles may be of a length, rigidity, density and number that will achieve the desired stiffness and precision in applying a substance to a dental surface, depending on the application.

While the present invention has been described and illustrated in conjunction with a number of specific embodiments, those skilled in the art will appreciate that variations and modifications may be made without departing from the principles of the inventions as herein illustrated, described and claimed.

The present invention may be embodied in other specific forms without departing from their spirit or characteristics. The described embodiments are to be considered in all respects as only illustrative, and not restrictive. The scope of the invention is, therefore, indicated by the appended claims, rather than the foregoing description. All changes that come within the meaning and range of equivalency of the claims are to be embraced within their scope.

What is claimed is:

1. A device for delivering and applying a dental substance to a dental surface comprising:
    a reservoir for holding a dental substance for later use by a dental practitioner,
    a plunger for exerting a force on dental substance located in said reservoir,
    a passageway having a proximal and a distal end, said passageway proximal end being located adjacent said reservoir, passageway having a similar cross sectional measurement the entirety of its length,
    an orifice located at said passageway distal end,
    a fiber tipped dental substance applicator, said applicator being installable in said orifice, said applicator including
        a body,
        a proximal end of said body,
        a distal end of said body,
        a plurality of pathways along said body running from said proximal end to said distal end of said body,
        a plurality of fibers located at said distal end of said body, said fibers being generally centrally located on said distal end of said body so that when said applicator is installed in said orifice, said fibers are generally centrally located with respect to said orifice;
    wherein pressing said plunger causes a quantity of dental substance to travel from said reservoir through said passageway and through said pathways to be dispensed adjacent said fibers so that said fibers may be use to apply said dental substance to a dental surface.

2. A device as recited in claim 1 further comprising a plurality of barbs located on the exterior periphery of said body for frictionally engaging passageway.

3. A device as recited in claim 1 further comprising a textured surface on the exterior periphery of said body for frictionally engaging said passageway.

4. A fiber tipped dental substance applicator comprising:
    a metal passageway having a proximal end and a distal end, said passageway having a similar cross sectional measurement the entirety of its length,
    an orifice located at said passageway distal end,
    an applicator end, said applicator end being installable in said orifice, said applicator end including
        a body,
        a proximal end of said body, a distal end of said body,
a plurality of pathways along said body running from said proximal end to said distal end of said body, and
a plurality of fibers located at said distal end of said body, said fibers being generally centrally located on said distal end of said body so that when said applicator end is installed in said orifice, said fibers are generally centrally located with respect to said orifice.

5. An applicator as recited in claim 4 further comprising a frictional engagement mechanism located on said body, said frictional engagement mechanism serving to frictionally engage said body in said metal passageway during use.

6. An applicator as recited in claim 5 wherein said frictional engagement mechanism is selected from the group consisting of hooks, lips and shelves.

7. An application as recited in claim 4 further comprising a smoothing bulb and wherein said fibers are fibers flocked on said smoothing bulb.

8. A method for applying a dental substance to a dental surface comprising the steps of:
obtaining a device for delivering and applying a dental substance to a dental surface that includes:
a reservoir for holding a dental substance for later use by a dental practitioner,
a plunger for exerting a force on dental substance located in said reservoir,
a passageway having a proximal and a distal end, said passageway proximal end being located adjacent said reservoir, passageway having a similar cross sectional measurement the entirety of its length,
an orifice located at said passageway distal end,
a fiber tipped dental substance applicator, said applicator being installable in said orifice, said applicator including
a body,
a proximal end of said body,
a distal end of said body,
a plurality of pathways along said body running from said proximal end to said distal end of said body,
a plurality of fibers located at said distal end of said body, said fibers being generally centrally located on said distal end of said body so that when said applicator is installed in said orifice, said fibers are generally centrally located with respect to said orifice;
depressing said plunger to cause a quantity of dental substance to travel from said reservoir through said passageway and through said pathways to be dispensed adjacent said fibers, and
using said fibers to apply said dental substance to a dental surface.

* * * * *